US005714594A

United States Patent [19]
Weinshilboum et al.

[11] Patent Number: 5,714,594
[45] Date of Patent: Feb. 3, 1998

[54] CDNA CLONING AND EXPRESSION OF HUMAN LIVER ESTROGEN SULFOTRANSFERASE

[75] Inventors: Richard M. Weinshilboum; Ibrahim A. Aksoy; Thomas C. Wood, all of Rochester, Minn.

[73] Assignee: Mayo Foundation for Medical Education and Research, Rochester, Minn.

[21] Appl. No.: 325,562

[22] Filed: Oct. 18, 1994

[51] Int. Cl.$^6$ .............................. C12N 15/54; C12N 9/10
[52] U.S. Cl. ................... 536/23.2; 536/23.1; 435/193; 435/320.1; 435/252.3; 435/240.2; 435/172.3
[58] Field of Search .......................... 536/23.1, 23.2; 435/193, 320.1, 252.3, 240.2, 172.3

[56] References Cited

PUBLICATIONS

I.A. Aksoy et al., "Cholesterol Sulfation in Human Liver: Catalysis by Dehydroepiandrosterone Sulfotransferase," *Drug Metab. Dispos.*, 21, 268–276 (1993).

I.A. Aksoy et al., "Human liver dehydroepiandrosterone sulfotransferase: Nature and extent of individual variation", *Clin. Pharmacol. Ther.*, 54, 498–506 (1993).

I.A. Askoy, et al., "Human Liver Estrogen Sulfotransferase: Identification by cDNA Cloning and Expression", *Biochem. and Biophys. Research Commun.* 200 1621–1629 (May 16, 1994).

I.A. Aksoy, et al., "Human Liver Estrogen Sulfotransferase (EST): Polymerase Chain Reaction (PCR) Cloning of cDNA", (Abstract) *ISSX Proc.*, 4, 181, 1993.

I.A. Aksoy, et al., "Human Liver Estrogen Sulfotransferase (EST): Polymerase Chain Reaction (PCR) Cloning of cDNA", (Poster Presentation for the Fifth North American Meeting of the International Society for the Study of Xenobiotics) Oct. 18, 1993.

I.A. Aksoy, et al., "Human Estrogen Sulfotransferase. cDNA Cloning, Expression and Characterization". (Abstract), *Proc. Amer. Assoc. Cancer. Res.*, 35, 276 (1994).

I.A. Aksoy, et al., "Human Estrogen Sulfotransferase: cDNA Cloning, Expression, and Characterization", (Poster Presentation for the Eighty–Fifth Annual Meeting of the American Association for Cancer Research (AACR)) Apr. 9–13, 1994.

I.A. Aksoy, "Pharmacogenetics of Human Liver Cytosolic Sulfotransferases: Biochemical and Molecular Studies" (May 1994).

R.J. Anderson, et al., "Phenolsulphotransferase in Human Tissue: Radiochemical Enzymatic Assay and Biochemical Properties", *Clin. Chim. Acta*, 103, 79–90 (1980).

R.T. Borchardt, et al., "An Ecteola–Cellulose Chromatography Assay for 3'–Phosphoadenosine 5'–Phosphosulfate: Phenol Sulfotransferase," *Anal. Biochem.*, 130, 334–338 (1983).

M.M. Bradford, "A Rapid and Sensitive Method for the Quantitation of Microgram Quantities of Protein Utilizing the Principle of Protein–Dye Binding," *Anal. Biochem.*, 72, 248–254 (1976).

N.R.C. Campbell et al., "Human Liver Phenol Sulfotransferase: Assay Conditions, Biochemical Properties and Partial Purification of Isozymes of the Thermostable Form," *Biochem. Pharmacol.*, 36, 1435–1446 (1987).

W.W. Cleland, "Computer Programmes for Processing Enzyme Kinetic Data," *Nature*, 198, 463–465 (1963).

C.N. Falany et al., "Purification and Characterization of Human Liver Dehydroepiandrosterone Sulphotransferase," *Biochem. J.*, 260, pp. 641–646 (1989).

A.A. Farooqui, "3'–Phosphoadenosine 5'–Phosphosulfate Metabolism in Mammalian Tissues," *Int. J. Biochem.*, 12, pp. 529–536 (1980).

A.P. Feinberg et al., "A Technique for Radiolabeling DNA Restriction Endonuclease Fragments to High Specific Activity," *Ana. Biochem.*, 132, 6–13 (1983).

Fiers et al., "Complete nucleodite sequence of SV40 DNA," *Nature*, 273, 113–120 (1978).

A. Foldes and J.L. Meek, "Rat Brain Phenolsulfotransferase–Partial Purification and Some Properties," *Biochem. Biophys. Acta*, 327, 365–373 (1973).

M.A. Frohman et al., "Rapid Production of Full–Length cDNAs from Rare Transcripts: Amplification Using a Single Gene–Specific Oligonucleotide Primer," *Proc. Nat'l. Acad. Sci. USA*, 85, 8998–9002 (1988).

F.L. Graham et al., "A New Technique for the Assay of Infectivity of Human Adenovirus 5 DNA," *Virology*, 52, 456–467 (1973).

F.L. Graham et al., "Characteristics of a Human Cell Line Transformed by DNA from Human Adenvirus Type 5," *J. Gen. Virol.*, 36, 59–72 (1977).

J.S. Hernandez et al., "Sulfation of Estrone and 17β–Estradiol in Human Liver: Catalysis by Thermostable Phenol Sulfotranferase and by Dehydroepiandrosterone Sulfotransferase," *Drug. Metab. Dispos.*, 20, 413–422 (1992).

R. Hobkirk, "Steroid Sulfation: Current Concepts," *Trends Endocrinol. Metab.*, 4, 69–74 (1993).

T. Honkasalo et al., "Determination of Phenol Sulphotransferase Activity by High–Performance Liquid Chromatography," *J. Chromatogr.*, 424, 136–140 (1988).

Hsiao et al., "High–frequency transformation of yeast by plasmids containing the cloned yeast ARG4 gene," *Proc. Natl. Acad. Sci. USA*, 76, 3829–3833 (1979).

W.B. Jakoby et al., "Sulfotransferases" in *Enzymatic Basis of Detoxication*; vol. II, W.B. Jakoby (ed), Academic Press: New York; pp. 199–229 (1980).

G.A. Johnson et al., "Sulfation of Minoxidil by Liver Sulfotransferase," *Biochem. Pharmacol.*, 31, 2949–2954 (1982).

(List continued on next page.)

*Primary Examiner*—Rebecca E. Prouty
*Attorney, Agent, or Firm*—Schwegman, Lundberg, Woessner & Kluth, P.A.

[57] ABSTRACT

The present invention provides an isolated and purified human DNA molecule consisting essentially of a DNA segment encoding an estrogen sulfotransferase protein or biologically active derivative thereof.

9 Claims, 7 Drawing Sheets

OTHER PUBLICATIONS

R.J. Kaufman, "Identification of the Components Necessary for Adenovirus Translational Control and Their Utilization in cDNA Expression Vectors," *Proc. Natl. Acad. Sci. USA*, 82, 689–693 (1985).

Kingsman et al., "Replication in *Saccharomyces cerevisiae* of Plasmid pBR313 Carrying DNA from the Yeast trpl Region," *Gene*, 7, 141–152 (1979).

A.-N.T. Kong et al., "Molecular Cloning of the Alcohol/Hydroxysteroid Form ($mST_{al}$) of Sulfotransferase from Mouse Liver," *Pharmaceut. Res.* 10, 627–630 (1993).

A.-N.T. Kong et al., "Molecular Cloning of cDNA Encoding the Phenol/Aryl Form of Sulfotransferase ($mST_{pl}$) from Mouse Liver," *Biochem. Biophys. Acta*, 1171, 315–318 (1993).

J. Langridge, "Genetic and Enzymatic Experiments Relating to the Tertiary Structure of β–Galactosidase," *J. Bacteriol.*, 96, 1711–1717 (1968).

C.C. Lee et al., "Generation of cDNA Probes Directed by Amino Acid Sequence: Cloning of Urate Oxidase," *Science*, 239, 1288–1291 (1988).

Luckow et al., "Trends in the Development of Baculovirus Expression Vectors," *Bio/Technology*, 6, 47–55 (1988).

H. Luthman et al., "High Efficiency Polyoma DNA Transfection of Chloroquine Treated Cells," *Nucleic Acids Res.*, 11, 1295–1308 (1983).

S. Maeda et al., "Production of Human α-Interferon in Silkworm using a Baculovirus Vector," *Nature*, 315, 592–594 (1985).

M.A. Mancini et al., "Spatio-Temporal Expression of Estrogen Sulfotransferase within the Hepatic Lobule of Male Rats: Implication of in Situ Estrogen Inactivation in Androgen Action," *Endocrinology*, 131, 1541–1546 (1992).

J. Mather et al., "Testicular Cell Culture," *Annals N.Y. Acad. Sci.*, 383, 44–68 (1982).

J. Mather, "Establishment and Characterization of Two Distinct Mouse Testicular Epithelial Cell Lines," *Biol. Reprod.*, 23, 243–252 (1980).

Alan Maxam et al., "Sequencing End–Labeled DNA with Base–Specific Chemical Cleavages," *Methods in Enzymology*, 65, 499–560 (1980).

J. Messing et al., "A System for Shotgun DNA Sequencing," *Nucl. Acids Res.*, 9, 309–321 (1981).

D. Miller et al., "An Insect Baculovirus Host–Vector System for High–Level Expression of Foreign Genes," *Genetic Engineering*, 8, 277–298 (1986).

G.J. Mulder et al., "Sulfation," in *Conjugation Reactions in Drug Metabolism;* Taylor & Francis Ltd.: New York; pp. 107–161 (1990).

R.C. Mulligan et al., "Expression of a Bacterial Gene in Mammalian Cells," *Science*, 209, 1422–1427 (1980).

D.M. Otterness et al., "Human Liver Dehydroepiandrosterone Sulfotransferase: Molecular Cloning and Expression of cDNA," *Mol. Pharmacol.*, 41, 865–872 (1992).

D.M. Otterness et al., "Human Liver Thermostable Phenol Sulfotransferase: Photoaffinity Labeling with 2–Iodo–4–Azidophenol," *Mol. Pharmacol.*, 36, 856–865 (1989).

G. Pavlakis et al., "Expression of Two Human Growth Hormone Genes in Monkey Cells Infected by Simian Virus 40 Recombinants," *Proc. Natl. Acad. Sci. USA*, 78, 7398–7402 (1981).

R.A. Price et al., "Genetic Polymorphism for Human Platelet Thermostable Phenol Sulfotransferase (TS PST) Activity," *Genetics*, 122, 905–914 (1989).

A. Radiminska et al., "Human Liver Steroid Sulphotransferase Sulphates Bile Acids," *Biochem. J.*, 272, 597–604 (1990).

G. Rein et al., "Multiple Forms of Phenolsulphotransferase in Human Tissues: Selective Inhibition by Dichloronitrophenol," *Biochem. Pharmacol.*, 31, 1893–1897 (1982).

C. Reiter et al., "Thermolabile and Thermostable Human Platelet Phenol Sulfotransferase: Substrate Specificity and Physical Separation," *Naunyn–Schmied. Archiv. Pharmacol.*, 324, 140–147 (1983).

J.I. Rotter et al., "A Genetic Component to the Variation of Dehydroepiandrosterone Sulfate," *Metabolism*, 34, 731–736 (1985).

A.K. Roy, "Regulation of Steroid Hormone Action in Target Cells by Specific Hormone-Inactivating Enzymes," *Proc. Soc. Exp. Biol. Med.*, 199, 265–272 (1992).

R.D. Sekura et al., "Assay of Sulfotransferases," *Analyt. Biochem.*, 95, 82–86 (1979).

F. Stahl et al., "Dehydroepiandrosterone (DHEA) Levels in Patients with Prostatic Cancer, Heart Diseases and Under Surgery Stress," *Exp. Clin. Endocrinol.*, 99, 68–70 (1992).

D.T. Stinchcomb et al., "Isolation and Characterisation of a Yeast Chromosomal Replicator," *Nature*, 282, 39–43 (1979).

R.S. Sundaram et al., "Human Intestinal Phenol Sulfotransferase: Assay Conditions, Activity Levels and Partial Purification of the Thermolabile Form," *Drug Metab. Dispos.*, 17, 255–264 (1989).

G. Tschumper et al., "Sequence of a Yeast DNA Fragment Containing a Chromosomal Replicator and TRP1 Gene," *Gene*, 10, 157–166 (1980).

L. Tseng et al., "Estrogen Sulfotransferase in Human Placenta," *J. Steroid Biochem.*, 22, 611–615 (1985).

G. Urlaub et al., *Proc. Natl. Acad. Sci. USA*, 77, 4216–4220 (1980).

P. Van Solingen et al., "Fusion of Yeast Spheroplasts," *J. Bact.*, 130, 946–947 (1977).

L. Varin et al., "Enzymatic Assay for Flavonoid Sulfotransferase," *Anal. Biochem.*, 161, 176–180 (1987).

L. Varin et al., "Molecular Characterization of Two Plant Flavonol Sulfotransferase," *Proc. Natl. Acad. Sci. USA*, 89, 1286–1290 (1992).

E. Wahle et al., "The Biochemistry of 3'–End Cleavage and Polyadenylation of Messenger RNA Precursors," *Ann. Rev. Biochem.*, 61, 419–440 (1992).

T. Watabe et al., "A 7–hydroxymethyl Sulfate Ester as an Active Metabolite of 7, 12–dimethylbenz[a]anthracene," *Science*, 215, 403–405 (1982).

R.M. Weinshilboum, *Genetic Strategies in Psychobiology and Psychiatry* (E.S. Gershon, S. Matthysse, X.O. Breakefield and R.D. Ciaranello, ed.) pp. 79–94; Boxwood Press, Pacific Grove, CA (1981).

R.M. Weinshilboum, "Sulfotransferase Pharmacogenetics," *Pharmacol. Ther.*, 45, 93–107 (1990).

R.M. Weinshilboum et al., "Sulfotransferase Enzymes," in *Conjugation–Deconjugation Reactions in Drug Metabolism and Toxicity;* Handbook of Experimental Pharmacology series; F.C. Kauffman, Ed.; Springer–Verlag (1994).

B. Wengle, "Studies on Ester Sulphates. 16. Use of $^{35}$S-labelled Inorganic Sulphate for Quantitative Studies of Sulphate Conjugation in Liver Extracts," *Acta. Chem. Scand.*, 18, 65–76 (1964).

R.M. Whittemore et al., "A Modified Ecteola Cellulose Assay for M and P Phenol Sulfotransferase," *Biochem. Pharmacol.*, 34, 1647–1652 (1985).

T.W. Wilborn et al., "Sequence Analysis and Expression of the cDNA for the Phenol–Sulfating Form of Human Liver Phenol Sulfotransferase," *Mol. Pharmacol.*, 43, 70–77 (1993).

G.N. Wilkinson, "Statistical Estimations in Enzyme Kinetics," *Biochem J.*, 80, 324–332 (1961).

G.G. Wong et al., "Human GM–CSF: Molecular Cloning of the Complementary DNA and Purification of the Natural and Recombinant Proteins," *Science*, 228, 810–815 (1985).

T.C. Wood et al., "Human Liver Thermolabile Phenol Sulfotransferase: cDNA Cloning, Expression and Characterization," *Biochem. Biophys. Res. Commun.*, 198, 1119–1127 (1994).

S.J. Gould et al., Use of the Polymerase Chain Reaction For Homology Probing: Isolation of Partial cDNA of Genomic Clones Encoding the Iron–Sulfur Protein os Succinate Dehydrogenase From Several Species, Proc. Natl. Acad. Sci. 86: 1934–1938, Mar. 1989.

T. Oeda et al., "Molecular Cloning and Expression of a Full Length Complementary DNA Encoding the Guinea Pig Adrenocortical Estrogen Sulfotransferase", Mol. Endocrinol. 6(8) 1216–1226, Aug. 1992.

W.F. Demyan et al., "Estrogen Sulfotransferase of the Rat Liver: Complementary DNA Cloning and Age– and Sex–Specific Regulation of Messenger RNA", Mol. Endocrinol. 6(4) 589–597, Apr. 1992.

A.R. Nash et al., "Oestrogen Sulfotransferase: Molecular Cloning and Sequencing of cDNA for the Bovine Placental Enzyme", Aust. J. Bio. Sci. 41(4) 507–516, 1988.

T. Hondoh et al., "Purification and Properties of Estrogen Sulfotransferase of Human Fetal Liver", Biomedical Research 14(2) 129–136, Apr. 1993.

K.J. Forbes–Bamforth et al., "Identification of a New Adult Human Liver Sulfotransferase With Specificity for Endogenous and Xenobiotic Estogens", Biochem. Biophys. Res. Commun. 198(2) 707–711, Jan. 1994.

HUMAN LIVER EST cDNA

```
-106  AGAAGTGGTTCTCATCTTTTTTTCCAGCTTAAGATCTGCCTTGGTATTTGAAGAGATATA   -47

-46  AACTAGATCAATTTCTTTCACAGGATCAACTAAACAGTGTACCACAATGAATTCTGAACT    14
                                                      M  N  S  E  L

15  TGACTATTATGAAAAGTTTGAAGAAGTCCATGGGATTCTAATGTATAAAGATTTTGTCAA    74
       D  Y  Y  E  K  F  E  E  V  H  G  I  L  M  Y  K  D  F  V  K

75  ATATTGGGATAATGTGGAAGCGTTCCAGGCAAGACCAGATGATCTTGTCATTGCCACCTA   134
       Y  W  D  N  V  E  A  F  Q  A  R  P  D  D  L  V  I  A  T  Y

135  CCCTAAATCTGGTACAACCTGGGTTAGTGAAATTGTGTATATGATCTATAAAGAGGGTGA   194
       P  K  S  G  T  T  W  V  S  E  I  V  Y  M  I  Y  K  E  G  D

195  TGTGGAAAAGTGCAAAGAAGATGTAATTTTTAATCGAATACCTTTCCTGGAATGCAGAAA   254
       V  E  K  C  K  E  D  V  I  F  N  R  I  P  F  L  E  C  R  K

255  AGAAAACCTCATGAATGGAGTAAAACAATTAGATGAGATGAATTCTCCTAGAATTGTGAA   314
       E  N  L  M  N  G  V  K  Q  L  D  E  M  N  S  P  R  I  V  K

315  GACTCATTTGCCACCTGAACTTCTTCCTGCCTCATTTTGGGAAAAGGATTGTAAGATAAT   374
       T  H  L  P  P  E  L  L  P  A  S  F  W  E  K  D  C  K  I  I

375  CTATCTTTGCCGGAATGCAAAGGATGTGGCTGTTTCCTTTTATTATTTCTTTCTAATGGT   434
       Y  L  C  R  N  A  K  D  V  A  V  S  F  Y  Y  F  F  L  M  V

435  GGCTGGTCATCCAAATCCTGGATCCTTTCCAGAGTTTGTGGAGAAATTCATGCAAGGACA   494
       A  G  H  P  N  P  G  S  F  P  E  F  V  E  K  F  M  Q  G  Q

495  GGTTCCTTATGGTTCCTGGTATAAACATGTAAAATCTTGGTGGGAAAAGGGAAAGAGTCC   554
       V  P  Y  G  S  W  Y  K  H  V  K  S  W  W  E  K  G  K  S  P

555  ACGTGTACTATTTCTTTTCTACGAAGACCTGAAAGAGGATATCAGAAAAGAGGTGATAAA   614
       R  V  L  F  L  F  Y  E  D  L  K  E  D  I  R  K  E  V  I  K

615  ATTGATACATTTCCTGGAAAGGAAGCCATCAGAGGAGCTTGTGGACAGGATTATACATCA   674
       L  I  H  F  L  E  R  K  P  S  E  E  L  V  D  R  I  I  H  H

675  TACTTCGTTCCAAGAGATGAAGAACAATCCATCCACAAATTACACAACACTGCCAGACGA   734
       T  S  F  Q  E  M  K  N  N  P  S  T  N  Y  T  T  L  P  D  E

735  AATTATGAACCAGAAATTGTCGCCCTTCATGAGAAAGGGAATTACAGGAGACTGGAAAAA   794
       I  M  N  Q  K  L  S  P  F  M  R  K  G  I  T  G  D  W  K  N

795  TCACTTTACAGTAGCCCTGAATGAAAAATTTGATAAACATTATGAGCAGCAAATGAAGGA   854
       H  F  T  V  A  L  N  E  K  F  D  K  H  Y  E  Q  Q  M  K  E

855  ATCTACACTGAAGTTTCGAACTGAGATCTAAGAAGGTCTTTCTTTACTTAACATATCTGA   914
       S  T  L  K  F  R  T  E  I  *

915  TATTAAAGATTTCTTTTCATTATTCAAAAAAAAAAAAAAAAAAA                   957
```

FIG. 2

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1063 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 107..989

( x i ) SEQUENCE DESCRIPTION: SEQ ID NO:1:

```
AGAAGTGGTT CTCATCTTTT TTTGCAGCTT AAGATCTGCC TTGGTATTTG AAGAGATATA        60

AACTAGATCA ATTTCTTTCA CAGGATCAAC TAAACAGTGT ACCACA ATG AAT TCT          115
                                                  Met Asn Ser
                                                   1

GAA CTT GAC TAT TAT GAA AAG TTT GAA GAA GTC CAT GGG ATT CTA ATG          163
Glu Leu Asp Tyr Tyr Glu Lys Phe Glu Glu Val His Gly Ile Leu Met
     5              10                  15

TAT AAA GAT TTT GTC AAA TAT TGG GAT AAT GTG GAA GCG TTC CAG GCA          211
Tyr Lys Asp Phe Val Lys Tyr Trp Asp Asn Val Glu Ala Phe Gln Ala
 20              25                  30                  35

AGA CCA GAT GAT CTT GTC ATT GCC ACC TAC CCT AAA TCT GGT ACA ACC          259
Arg Pro Asp Asp Leu Val Ile Ala Thr Tyr Pro Lys Ser Gly Thr Thr
             40                  45                  50

TGG GTT AGT GAA ATT GTG TAT ATG ATC TAT AAA GAG GGT GAT GTG GAA          307
Trp Val Ser Glu Ile Val Tyr Met Ile Tyr Lys Glu Gly Asp Val Glu
         55                  60                  65

AAG TGC AAA GAA GAT GTA ATT TTT AAT CGA ATA CCT TTC CTG GAA TGC          355
Lys Cys Lys Glu Asp Val Ile Phe Asn Arg Ile Pro Phe Leu Glu Cys
             70                  75                  80

AGA AAA GAA AAC CTC ATG AAT GGA GTA AAA CAA TTA GAT GAG ATG AAT          403
Arg Lys Glu Asn Leu Met Asn Gly Val Lys Gln Leu Asp Glu Met Asn
         85                  90                  95

TCT CCT AGA ATT GTG AAG ACT CAT TTG CCA CCT GAA CTT CTT CCT GCC          451
Ser Pro Arg Ile Val Lys Thr His Leu Pro Pro Glu Leu Leu Pro Ala
100                 105                 110                 115

TCA TTT TGG GAA AAG GAT TGT AAG ATA ATC TAT CTT TGC CGG AAT GCA          499
Ser Phe Trp Glu Lys Asp Cys Lys Ile Ile Tyr Leu Cys Arg Asn Ala
                120                 125                 130

AAG GAT GTG GCT GTT TCC TTT TAT TAT TTC TTT CTA ATG GTG GCT GGT          547
Lys Asp Val Ala Val Ser Phe Tyr Tyr Phe Phe Leu Met Val Ala Gly
            135                 140                 145

CAT CCA AAT CCT GGA TCC TTT CCA GAG TTT GTG GAG AAA TTC ATG CAA          595
His Pro Asn Pro Gly Ser Phe Pro Glu Phe Val Glu Lys Phe Met Gln
        150                 155                 160

GGA CAG GTT CCT TAT GGT TCC TGG TAT AAA CAT GTA AAA TCT TGG TGG          643
Gly Gln Val Pro Tyr Gly Ser Trp Tyr Lys His Val Lys Ser Trp Trp
165                 170                 175

GAA AAG GGA AAG AGT CCA CGT GTA CTA TTT CTT TTC TAC GAA GAC CTG          691
Glu Lys Gly Lys Ser Pro Arg Val Leu Phe Leu Phe Tyr Glu Asp Leu
180                 185                 190                 195

AAA GAG GAT ATC AGA AAA GAG GTG ATA AAA TTG ATA CAT TTC CTG GAA          739
Lys Glu Asp Ile Arg Lys Glu Val Ile Lys Leu Ile His Phe Leu Glu
```

|  |  |  |  |  |  |  |  |  |  |  |  |  |  |  |  |
|---|---|---|---|---|---|---|---|---|---|---|---|---|---|---|---|
| AGG | AAG | CCA | TCA | GAG | GAG | CTT | GTG | GAC | AGG | ATT | ATA | CAT | CAT | ACT | TCG |
| Arg | Lys | Pro | Ser 215 | Glu | Glu | Leu | Val | Asp 220 | Arg | Ile | Ile | His | His 225 | Thr | Ser |

787

|  |  |  |  |  |  |  |  |  |  |  |  |  |  |  |  |
|---|---|---|---|---|---|---|---|---|---|---|---|---|---|---|---|
| TTC | CAA | GAG | ATG | AAG | AAC | AAT | CCA | TCC | ACA | AAT | TAC | ACA | ACA | CTG | CCA |
| Phe | Gln | Glu 230 | Met | Lys | Asn | Asn | Pro 235 | Ser | Thr | Asn | Tyr 240 | Thr | Thr | Leu | Pro |

835

|  |  |  |  |  |  |  |  |  |  |  |  |  |  |  |  |
|---|---|---|---|---|---|---|---|---|---|---|---|---|---|---|---|
| GAC | GAA | ATT | ATG | AAC | CAG | AAA | TTG | TCG | CCC | TTC | ATG | AGA | AAG | GGA | ATT |
| Asp | Glu 245 | Ile | Met | Asn | Gln | Lys 250 | Leu | Ser | Pro | Phe | Met 255 | Arg | Lys | Gly | Ile |

883

|  |  |  |  |  |  |  |  |  |  |  |  |  |  |  |  |
|---|---|---|---|---|---|---|---|---|---|---|---|---|---|---|---|
| ACA | GGA | GAC | TGG | AAA | AAT | CAC | TTT | ACA | GTA | GCC | CTG | AAT | GAA | AAA | TTT |
| Thr 260 | Gly | Asp | Trp | Lys | Asn 265 | His | Phe | Thr | Val | Ala 270 | Leu | Asn | Glu | Lys | Phe 275 |

931

|  |  |  |  |  |  |  |  |  |  |  |  |  |  |  |  |
|---|---|---|---|---|---|---|---|---|---|---|---|---|---|---|---|
| GAT | AAA | CAT | TAT | GAG | CAG | CAA | ATG | AAG | GAA | TCT | ACA | CTG | AAG | TTT | CGA |
| Asp | Lys | His | Tyr 280 | Glu | Gln | Gln | Met | Lys 285 | Glu | Ser | Thr | Leu | Lys 290 | Phe | Arg |

979

|  |  |  |  |
|---|---|---|---|
| ACT | GAG | ATC | T AAGAAGGTCT TTCTTTACTT AACATATCTG ATATTAAAGA |
| Thr | Glu | Ile |  |

1029

TTTCTTTTCA TTATTCAAAA AAAAAAAAAA AAAA

1063

( 2 ) INFORMATION FOR SEQ ID NO:2:

( i ) SEQUENCE CHARACTERISTICS:
        ( A ) LENGTH: 294 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met 1 | Asn | Ser | Glu | Leu 5 | Asp | Tyr | Tyr | Glu | Lys 10 | Phe | Glu | Glu | Val | His 15 | Gly |
|---|---|---|---|---|---|---|---|---|---|---|---|---|---|---|---|
| Ile | Leu | Met | Tyr 20 | Lys | Asp | Phe | Val | Lys 25 | Tyr | Trp | Asp | Asn | Val 30 | Glu | Ala |
| Phe | Gln | Ala 35 | Arg | Pro | Asp | Asp | Leu 40 | Val | Ile | Ala | Thr | Tyr 45 | Pro | Lys | Ser |
| Gly | Thr 50 | Thr | Trp | Val | Ser | Glu 55 | Ile | Val | Tyr | Met | Ile 60 | Tyr | Lys | Glu | Gly |
| Asp 65 | Val | Glu | Lys | Cys | Lys 70 | Glu | Asp | Val | Ile | Phe 75 | Asn | Arg | Ile | Pro | Phe 80 |
| Leu | Glu | Cys | Arg | Lys 85 | Glu | Asn | Leu | Met | Asn 90 | Gly | Val | Lys | Gln | Leu 95 | Asp |
| Glu | Met | Asn | Ser 100 | Pro | Arg | Ile | Val | Lys 105 | Thr | His | Leu | Pro | Pro 110 | Glu | Leu |
| Leu | Pro | Ala 115 | Ser | Phe | Trp | Glu | Lys 120 | Asp | Cys | Lys | Ile | Ile 125 | Tyr | Leu | Cys |
| Arg | Asn 130 | Ala | Lys | Asp | Val | Ala 135 | Val | Ser | Phe | Tyr | Tyr 140 | Phe | Phe | Leu | Met |
| Val 145 | Ala | Gly | His | Pro | Asn 150 | Pro | Gly | Ser | Phe | Pro 155 | Glu | Phe | Val | Glu | Lys 160 |
| Phe | Met | Gln | Gly | Gln 165 | Val | Pro | Tyr | Gly | Ser 170 | Trp | Tyr | Lys | His | Val 175 | Lys |
| Ser | Trp | Trp | Glu 180 | Lys | Gly | Lys | Ser | Pro 185 | Arg | Val | Leu | Phe | Leu 190 | Phe | Tyr |
| Glu | Asp | Leu 195 | Lys | Glu | Asp | Ile | Arg 200 | Lys | Glu | Val | Ile | Lys 205 | Leu | Ile | His |
| Phe | Leu 210 | Glu | Arg | Lys | Pro | Ser 215 | Glu | Glu | Leu | Val | Asp 220 | Arg | Ile | Ile | His |

```
His  Thr  Ser  Phe  Gln  Glu  Met  Lys  Asn  Asn  Pro  Ser  Thr  Asn  Tyr  Thr
225                      230                 235                           240

Thr  Leu  Pro  Asp  Glu  Ile  Met  Asn  Gln  Lys  Leu  Ser  Pro  Phe  Met  Arg
                    245                      250                      255

Lys  Gly  Ile  Thr  Gly  Asp  Trp  Lys  Asn  His  Phe  Thr  Val  Ala  Leu  Asn
               260                      265                      270

Glu  Lys  Phe  Asp  Lys  His  Tyr  Glu  Gln  Gln  Met  Lys  Glu  Ser  Thr  Leu
          275                 280                      285

Lys  Phe  Arg  Thr  Glu  Ile
290
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Pro  Xaa  Ser  Phe  Trp  Glu  Lys
1                    5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
His  Tyr  Glx  Gln  Gln  Met  Lys
1                    5
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
CCAG Y MTCAT  TTTGGGAAAA                                                    20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
TTCATTTGCT  GCTSRTAGTG                                                      20
```

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CCTGTCCTTG CATGAATTTC TCCAC     25

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GATAGATTAT CTTACAA     17

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CACGAATTCA CTATCGATTC TGGAACCTTC AGAGG     35

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTGGTTCGGC CCACCTCTGA AGGTTCCAGA ATCGATAG     38

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GGGAAAGAGT CCACGTGT     18

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:12:

CCATCAGAGG AGCTTGTGGA CAGG    24

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

AACTGGAAGA ATTCGCGGCC GCAGGAATTT TTTTTTTTTT TTTTT    45

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AGTCCAATTG CAGTGTACCA CAATGAATTC TG    32

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GACTCAATTG CCTTCTTAGA TCTCAGTTCG AA    32

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

Tyr Pro Lys Ser Gly Thr Xaa Trp
  1               5

( 2 ) INFORMATION FOR SEQ ID NO:17:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

Arg Lys Gly Xaa Xaa Gly Asp Trp Lys Asn Xaa Phe Thr
1               5                   10

CDNA CLONING AND EXPRESSION OF HUMAN LIVER ESTROGEN SULFOTRANSFERASE

BACKGROUND OF THE INVENTION

The metabolism of many drugs, xenobiotics, neurotransmitters and hormones includes a step involving the enzymatic addition of a sulfate ($SO_4^{-2}$) group. The addition of a sulfate group is commonly referred to as sulfate conjugation, or simply sulfation. The enzymes responsible for sulfate conjugation are known as sulfotransferases, as they act by transferring a sulfate group from one biological molecule (the sulfate donor) to another (the sulfate acceptor) in a sulfotransferase reaction.

Human liver tissue is known to catalyze a number of sulfotransferase reactions, all of which utilize 3'-phosphoadenosine-5'-phosphosulfate (PAPS) as a sulfate donor (G. J. Mulder et al., *Conjugation Reactions in Drug Metabolism*, 107–161, Taylor & Francis Ltd., New York (1990)). Specific cytosolic sulfotransferase enzymes that are present in human liver include dehydroepiandrosterone sulfotransferase (DHEA ST) and two forms of phenol sulfotransferase (PST), known as thermolabile PST (TL PST) and thermostabile PST (TS PST).

These three enzymes can be characterized and classified by their thermostability, their sensitivity to inhibition by 2,6-dichloro-4-nitrophenol (DCNP), a competitive inhibitor of some types of sulfotransferase activity, and by their preferred substrates. DHEA ST catalyzes the sulfate conjugation of cholesterol, bile acids and steroid hormones. It is relatively thermostable and is resistant to DCNP inhibition. TL PST is also resistant to DCNP inhibition but is, as its name indicates, thermolabile. This sulfotransferase preferentially catalyzes the sulfate conjugation of micromolar concentrations of dopamine and other phenolic monoamines. In contrast, TS PST is thermostabile, sensitive to DCNP inhibition, and catalyzes the sulfation of micromolar concentrations of simple planar phenols such as 4-nitrophenol.

Estrogens are not preferred substrates for any of these three human liver sulfotransferases. Only two (DHEA ST and TS PST) are even capable of catalyzing the sulfation of estrogens. Sulfotransferases specific for estrogen (estrogen sulfotransferases, or "ESTs") are, however, known for several nonhuman species (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol.*, 6, 1216–1226 (1992)), and show a high degree of sequence homology. Pairwise comparisons between the amino acid sequences of ESTs in rat liver, bovine placenta and guinea pig adrenal cortex show a high level of identity (66–70%). This suggests that mammalian ESTs may be members of a subfamily within a sulfotransferase gene superfamily—a subfamily distinct from those to which the PSTs and DHEA ST belong. It has been suggested that differences in the formation of estrogen sulfates might play a role in variation in response to various estrogens and other structurally-related therapeutic agents (R. Hobkirk, *Trends Endocrinol. Metab.*, 4, 69–74 (1993); A. K. Roy, *Proc. Soc. Exp. Biol. Med.*, 199, 265–272 (1992); M. A. Mancini et al., *Endocrinology*, 131, 1541–1546 (1992)). It would be a significant medical advance to discover, clone, and characterize a human EST complementary DNA (cDNA).

To date, vigorous genetic engineering efforts in the field of sulfate metabolism have resulted in the cloning and expression of cDNAs for several sulfotransferases: human liver DHEA ST (D. M. Otterness et al., *Mol. Pharmacol.*, 41, 865–872 (1992)), TS PST (W. Wilborn et al., *Mol. Pharmacol.*, 43, 70–77 (1993)), TL PST (T. C. Wood et al., *Biochem. Biophys. Res. Commun.*, 198, 1119–1127 (1994)) and a group of ESTs isolated from several tissues of non-human mammalian species (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol.*, 6, 1216–1226 (1992)). No group has yet identified or cloned a human estrogen sulfotransferase cDNA.

Estrogen sulfotransferase activity has been detected in human liver (K. J. Forbes-Bamforth et al., *Biochem. Biophys. Res. Commun.*, 198, 707–711 (1994). However, a human EST cDNA was not isolated. Identification of a human estrogen sulfotransferase cDNA, and production of human estrogen sulfotransferase, would be useful in the determination of which endogenous steroid hormones and/or drugs might be metabolized by the protein encoded by the cDNA. Therefore, what is needed is a DNA molecule that encodes human estrogen sulfotransferase.

BRIEF DESCRIPTION OF THE FIGURES

FIG. 2. Human liver EST cDNA nucleotide and deduced amino acid sequence. SEQ ID NO:1 and SEQ ID NO:2 nucleotides are numbered in the 5' to 3' direction with the adenosine of the translation initiation codon designated as +1. The polyadenylation signal sequence ATTAAA is underlined.

SUMMARY OF THE INVENTION

Figure 1:
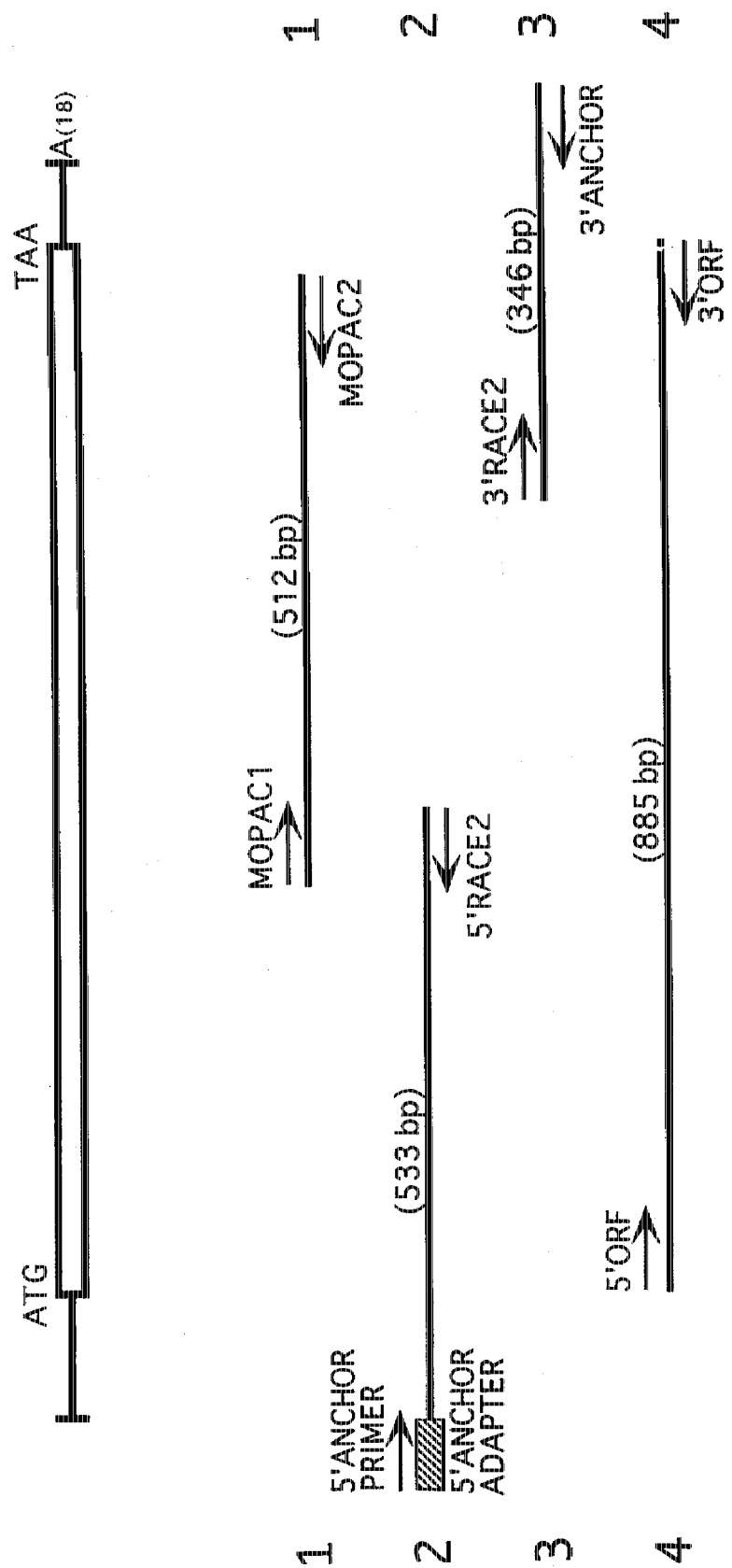
FIG. 1. Cloning strategy for human liver EST cDNA. The full-length human liver EST cDNA is depicted at the top of the diagram in which the box represents the open reading frame (ORF), while solid lines represent the 5'- and 3'-untranslated regions (UTRs). Oligonucleotide primers used in the invention are schematically represented by arrows, and PCR amplification products are schematically represented by the solid lines associated with each primer pair.

The present invention provides an isolated and purified human DNA molecule consisting essentially of a DNA segment encoding an estrogen sulfotransferase protein or biologically active derivative thereof. Preferably, the DNA molecule is cDNA. In particularly preferred embodiments, the protein is represented by the amino acid sequence SEQ ID NO:2 shown in FIG. 2 and the DNA molecule is represented by the nucleotide sequence SEQ ID NO:1 shown in FIG. 2.

DETAILED DESCRIPTION OF THE INVENTION

Specifically, the present invention is directed to the cloning and expression of human estrogen sulfotransferase cDNA as well as the characterization and production of a human estrogen sulfotransferase (EST). To that end, the invention provides an isolated and purified human DNA molecule consisting essentially of a DNA segment encoding a human estrogen sulfotransferase (EST) protein or biologically active derivative thereof. More preferably, the cDNA molecule encodes the protein represented by the amino acid sequence SEQ. ID NO:2 shown in FIG. 2. Most preferably, the cDNA molecule is represented by the complete nucleotide sequence SEQ ID NO:1 shown in FIG. 2. Isolated and purified peptides encoded by this DNA which are biologically active are also within the scope of the invention.

As used herein, the terms "isolated and purified" refer to in vitro isolation of a DNA molecule or peptide from its natural cellular environment, and from association with other coding regions of the human genome, so that it can be sequenced, replicated, and/or expressed. Preferably, the isolated and purified DNA molecules of the invention comprise a single coding region. Thus, the present DNA molecules are those "consisting essentially of" a DNA segment encoding an estrogen sulfotransferase protein or biologically active derivative thereof. Although the DNA molecule includes a single coding region, it can contain additional nucleotides that do not detrimentally affect the function of the DNA molecule, i.e., the expression of the estrogen sulfotransferase protein or biologically active derivative thereof. For example, the 5' and 3' untranslated regions may contain variable numbers of nucleotides. Preferably, additional nucleotides are outside the single coding region.

The present invention also provides an isolated and purified DNA molecule that encodes an estrogen sulfotransferase protein and that hybridizes to a DNA molecule complementary to the DNA molecule shown in FIG. 2 under high stringency hybridization conditions. As used herein, "high stringency hybridization conditions" refers to at least about 60° C., 0.1% SDS, 0.5×SSC.

The present invention also provides an isolated and purified (preferably chemically synthesized) oligonucleotide of at least seven nucleotides (i.e., a primer or a probe preferably containing no more than 300 nucleotides) which hybridizes to the DNA molecules of the present invention, preferably the cDNA molecule shown in FIG. 2, under high stringency hybridization conditions. Oligonucleotide probes and primers are segments of labeled, single-stranded DNA which will hybridize, or noncovalently bind, with complementary single-stranded DNA to be identified. If desired, the probe and primer can be labeled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe or primer may also be labeled at both ends with different types of labels for ease of separation, as, for example, by using an isotopic label at one end and a biotin label at the other end.

As used herein, the term "estrogen sulfotransferase protein" refers to a sulfotransferase enzyme that shows preference for estrone as a sulfation substrate over the other common sulfotransferase substrates. DHEA, 4-nitrophenol, or dopamine. A "biologically active derivative thereof" is a human estrogen sulfotransferase that is modified by amino acid deletion, addition, substitution, or truncation, or that has been chemically derivatized, but that nonetheless utilizes estrogen as its preferred sulfate-acceptor substrate, and sulfates estrone at a higher level than it sulfates DHEA, 4-nitrophenol, or dopamine. For example, it is known in the art that substitutions of aliphatic amino acids such as alanine, valine and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "biologically active derivative" is intended to include ESTs as thus modified. The term also includes fragments, variants, analogs or chemical derivatives of human EST. The term "fragment" is meant to refer to any polypeptide subset of human EST. Fragments can be prepared by subjecting human EST to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire human EST molecule or to a fragment thereof. A molecule is said to be "substantially similar" to EST or a fragment thereof if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess estrogen sulfotransferase activity, they are considered variants as that term is used herein even if the structure of one of the molecules is not found in the other, or if the sequences of amino acid residues are not identical. The term "analog" is meant to refer to a protein that differs structurally from the wild type enzyme EST, but possesses sulfotransferase activity utilizing estrogen as a preferred substrate.

The present invention also provides a vector comprising an isolated and purified DNA molecule encoding human estrogen sulfotransferase or a biologically active derivative thereof, preferably the sulfotransferase having the amino acid sequence SEQ ID NO:2 of FIG. 2. Preferably, the vector includes a single estrogen sulfotransferase coding region as well as a second DNA segment operably linked to the coding sequence and capable of directing expression of human estrogen sulfotransferase, such as a promoter region operably linked to the 5' end of the coding DNA sequence. The vector can also include a DNA segment that is a selectable marker gene or a reporter gene.

The identification of a human EST cDNA allows for the ability to determine which endogenous steroid hormones and/or drugs might be metabolized by the protein encoded by the cDNA. Using standard biochemical procedures well-known in the art, oligonucleotide probes can be used to detect and amplify an EST cDNA molecule in a wide variety of biological samples, including, for example, tissue, and cultured cells. For example, Southern or Northern blotting hybridization techniques using labeled probes can be used. Alternatively, PCR techniques can be used. Nucleic acid sequencing of amplified PCR products can be used to detect mutations in the EST cDNA.

Detection of the EST cDNA can involve the use of the polymerase chain reaction sequence amplification method (PCR) using novel primers. The method involves treating extracted DNA to form single-stranded complementary strands, treating the separate complementary strands of DNA with two oligonucleotide primers, extending the primers to form complementary extension products that act as templates for synthesizing the desired nucleic acid molecule; and detecting the amplified molecule.

DNA primer pairs of known sequence positioned 10–300 base pairs apart that are complementary to the plus and minus strands of the DNA to be amplified can be prepared by well known techniques for the synthesis of oligonucleotides. Conveniently, one end of each primer can be extended and modified to create restriction endonuclease sites when the primer is annealed to the target DNA. These restriction sites facilitate the use of the amplified product for cloning at a later date. The PCR reaction mixture can contain the target DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Preferred primer pairs include 5'ORF/3'ORF and MoPAC1/MoPAC2 and are shown in FIG. 1. MoPAC1 and MoPAC2 are each doubly degenerate primers, insofar as at two positions in each of them, two different amino acids are incorporated at those locations (see Table 1). These primers can be used in various combinations or with any other primer that can be designed to hybridize to a portion of DNA such that the amplified product contains all or part of a sequence encoding EST.

Cloning of the open reading frame encoding EST into the appropriate replicable vectors allows expression of the gene product, EST, and makes the coding region available for further genetic engineering. Expression of EST or portions thereof, is useful because these gene products can be used as antigens to produce antibodies, as described in more detail below.

1. Isolation of DNA

DNA containing the region encoding EST may be obtained from any cDNA library prepared from tissue believed to possess the EST mRNA and to express it at a detectable level. Preferably, the cDNA library is derived from human liver or fetal tissue. Alternatively, the region encoding EST may be obtained from a genomic DNA library or by in vitro polynucleotide synthesis from the complete nucleotide acid sequence.

Libraries are screened with appropriate probes designed to identify the cDNA of interest. Preferably, for cDNA libraries, suitable probes include oligonucleotides that consist of known or suspected portions of the EST cDNA from the same or different species; and/or complementary or homologous cDNAs or fragments thereof that consist of the same or a similar DNA. For cDNA expression libraries (which express the protein), suitable probes include monoclonal or polyclonal antibodies that recognize and specifically bind to the EST protein. Appropriate probes for screening cDNA libraries include, but are not limited to, oligonucleotides, cDNAs, or fragments thereof that consist of the same or a similar gene, and/or homologous genomic DNAs or fragments thereof. Screening the cDNA library with the selected probe may be accomplished using standard procedures.

Screening cDNA libraries using synthetic oligonucleotides as probes is a preferred method of practicing this invention. The oligonucleotide sequences selected as probes should be of sufficient length and sufficiently unambiguous to minimize false positives. The actual nucleotide sequence(s) of the probe(s) is usually designed based on regions of the EST cDNA that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the EST nucleic acid that encodes a full-length mRNA transcript, including the complete coding region for the gene product, EST. Nucleic acid containing the complete coding region can be obtained by screening selected cDNA libraries using the deduced amino acid sequence.

An alterative means to isolate the DNA encoding EST is to use PCR methodology. This method requires the use of oligonucleotide primer probes that will hybridize to the DNA encoding EST. Strategies for selection of PCR primer oligonucleotides are described below.

2. Insertion of DNA into Vector

The nucleic acid containing the EST coding region is preferably inserted into a replicable vector for further cloning (amplification of the DNA) or for expression of the gene product, EST. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. For example, a vector is cloned in *E. coli* and then the same vector is transfected into yeast or mammalian cells for expression even though it is not capable of replicating independently of the host cell chromosome. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmids or DNA fragments are cleaved, tailored, and relegated in the form desired to generate the plasmids required. Typically, the ligation mixtures are used to transform *E. coli* K12 strain 294 (ATCC 31,446) and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9, 309 (1981) and Maxam et al., *Methods in Enzymology*, 65, 499 (1980).

Replicable cloning and expression vector components generally include, but are not limited to, one or more of the following: a signal sequence, an origin of replication, one or more marker genes, an enhancer element, a promoter and a transcription termination sequence.

Vector component: signal sequence. A signal sequence may be used to facilitate extracellular transport of a cloned protein. To this end, the EST gene product, EST, may be expressed not only directly, but also as a fusion product with a heterologous polypeptide, preferably a signal sequence or other polypeptide having a specific cleavage site at the N-terminus of the cloned protein or polypeptide. The signal sequence may be a component of the vector, or it may be a part of the EST DNA that is inserted into the vector. The heterologous signal sequence selected should be one that is recognized and processed (i.e., cleaved by a signal peptidase) by the host cell. For prokaryotic host cells, a prokaryotic signal sequence may be selected, for example, from the group of the alkaline phosphatase, penicillinase, lpp or heat-stable intertoxin II leaders. For yeast secretion, the signal sequence used may be, for example, the yeast invertase, alpha factor, or acid phosphatase leaders. In mammalian cell expression, a native signal sequence may be satisfactory, although other mammalian signal sequences may be suitable, such as signal sequences from secreted polypeptides of the same or related species, as well as viral secretory leaders, for example, the herpes simplex gD signal.

Vector component: origin of replication. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Vector component: marker gene. Expression and cloning vectors may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene express a protein conferring drug resistance and thus survive the selection regimen.

An example of suitable selectable markers for mammalian cells are those that enable the identification of cells competent to take up the EST nucleic acid, such as dihydrofolate reductase (DHFR) or thymidine kinase. The mammalian cell transformants are placed under selection pressure that only transformants are uniquely adapted to survive by virtue of having taken up the marker. For example, cells transformed with the DHFR selection gene are first identified by culturing all the transformants in a culture medium that contains methotrexate, a competitive antagonist for DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77, 4216 (1980). The transformed cells are then exposed to increased levels of methotrexate. This leads to the synthesis of multiple copies of the DHFR gene, and, concomitantly, multiple copies of the other DNA comprising the expression vectors, such as the EST cDNA. This amplification technique can be used with any otherwise suitable host, e.g., ATCC No. CCL61 CHO-K1, notwithstanding the presence of endogenous DHFR if, for example, a mutant DHFR gene that is highly resistant to methotrexate is employed. Alternatively, host cells (particularly wild-type hosts that contain endogenous DHFR) transformed or co-transformed with EST DNA, wild-type DHFR protein, and another selectable marker such as aminoglycoside 3' phosphotransferase (APH) can be selected by cell growth in a medium containing a selection agent for the selectable marker such as an aminoglycosidic antibiotic, e.g., kanamycin or neomycin. A suitable selection gene for use in yeast is the trp1 gene present in the yeast plasmid YRp7 (Stinchcomb et al., *Nature*, 282, 39 (1979); Kingsman et al., *Gene*, 7, 141 (1979); or Tschemper et al., *Gene*, 10, 157 (1980)). The trp1 gene provides a selection marker for a mutant strain of yeast lacking the ability to grow in tryptophan, for example, ATCC NO. 44076 or PEP4-1 (Jones, *Genetics*, 85, 12 (1977)). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Vector component: promoter. Expression and cloning vectors usually contain a promoter that is recognized by the host organism and is operably linked to the EST nucleic acid. Promoters are untranslated sequences located upstream (5') to the start codon of a structural gene (generally within about 100 to 1000 bp) that control the transcription and translation of a particular nucleic acid sequence, such as the EST nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time, a large number of promoters recognized by a variety of potential host cells are well known in the art. Promoters are removed from their source DNA using a restriction enzyme digestion and inserted into the cloning vector using standard molecular biology techniques. Native or heterologous promoters can be used to direct amplification and/or expression of EST DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to EST DNA using linkers or adapters to supply any required restriction sites. Promoters for use in bacterial systems may contain a Shine-Dalgarno sequence for RNA polymerase binding.

Promoter sequences are known for eukaryotes. Virtually all eukaryotic genes have an AT-rich region located approximately 25 to 30 bp upstream from the site where transcription is initiated. Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

EST transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, Hepatitis-B virus and most preferably Simian Virus 40 (SV40) (Fiers et al., *Nature*, 273, 113 (1978); Mulligan et al., *Science*, 209, 1422–1427 (1980); Pavlakis et al., *Proc. Natl. Acad. Sci. USA*, 78, 7398–7402 (1981)). Heterologous mammalian promoters (e.g., the actin promoter or an immunoglobulin promoter) and heat-shock promoters can also be used, as can the promoter normally associated with the EST sequence itself, provided such promoters are compatible with the host cell systems.

Vector component: enhancer element. Transcription of EST DNA by higher eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to the transcription unit, within an intron as well as within the coding sequence itself. Many enhancer sequences are now known from mammalian genes (globin, elastase, albumin, alpha-fetoprotein, and insulin). Typically, however, an enhancer from a eukaryotic cell virus will be used. Examples include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the EST cDNA, but is preferably located at a site 5' of the promoter.

Vector component: transcription termination. Expression vectors used in eukaryotic host cells (yeast, fungi, insect, plant, animal, human or nucleated cells from other multicellular organisms) can also contain sequences necessary for the termination of transcription and for stabilizing the mRNA. Such sequences are commonly available from the 5' and, occasionally, 3' untranslated regions of eukaryotic or viral DNAs or cDNAs. These regions can contain nucleotide segments transcribed as polyadenylated fragments in the untranslated portion of mRNA encoding EST.

Also useful are expression vectors that provide for transient expression in mammalian cells of EST DNA. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of ataxin-1 that have wild-type or variant biological activity.

The genetically engineered plasmid of the invention can be used to transform a host cell. Typically, eukaryotic host cells are used in the expression system according to the invention, although prokaryotic cells may also be used. Preferably, COS-1 cells are transformed with the genetically engineered plasmid of the invention.

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcsecans*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for EST-encoding vectors. *Saccaromyces cerevisiae*, or common baker's yeast, is the most commonly used among lower eukaryotic host microorganisms. However, a number of other genera, species, and strains are commonly available and useful herein, such as *Schizosaccaromyces pombe*, Kluyveromyces hosts such as, e.g., *K. lactis*, *K. fragilis*, *K. bulgaricus*, *K. thermotolerans*, and *K. marxianus*, *yarrowia*, *Pichia pastoris*, Candida, *Trichoderma reesia*, *Neurospora crassa*, and filamentous fungi such as, e.g., Neurospora, Penicillium, Tolypocladium, and Aspergillus hosts such as *A. nidulans*.

Suitable host cells for the expression of glycosylated EST are derived from multicellular organisms. Such host cells are capable of complex processing and glycosylation activities. In principle, any higher eukaryotic cell culture is workable, whether from vertebrate or invertebrate culture. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6, 47–55 (1988); Miller et al., *Genetic Engineering*, 8, 277–279 (1986); and Maeda et al., *Nature*, 315, 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Vertebrate cells can also be used as hosts. Propagation of vertebrate cells in culture (tissue culture) has become a routine procedure in recent years. Examples of useful mammalian host cell lines are monkey kidney CV1 line transformed by SV40 (CAS-7, ATCC CRL-1651); human embryonic kidney line (293 or 293 cells subcloned for growth in suspension culture, Graham et al., *J. Gen. Virol.*, 36, 59 (1977)); baby hamster kidney cells (BHK, ATCC CCL 10); Chinese hamster ovary cells/-DHFR (CHO, Urlaub and Chasin, *Proc. Natl. Acad. Sci. USA*, 77, 4216 (1980)); mouse sertoli cells (TM4, Mather, *Biol. Reprod.*, 23, 243–251 (1980)); monkey kidney cells (CV1 ATCC CCL 70); African green monkey kidney cells (VERO-76, ATCC CRL-1587);

human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL 51); TRI cells (Mather et al., *Annals N.Y. Acad. Sci.*, 383, 44–68 (1982)); MRC 5 cells; FS4 cells; and a human hepatoma line (Hep G2).

In a preferred embodiment of the invention, the eukaryotic host cell COS-1 is transformed with the eukaryotic expression vector p91023(B), into which a cDNA molecule encoding human estrogen sulfotransferase has been subcloned. The transformed COS-1 host cells of the invention are grown, expression of estrogen sulfotransferase is induced, and the cells are harvested and processed using methods and procedures well-known in the art. This genetically engineered expression system provided by the invention is thus a convenient source of human estrogen sulfotransferase.

4. Transfection and Transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequence are in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. Calcium chloride is generally used for prokaryotes or other cells that contain substantial cell-wall barriers. For mammalian cells without cell walls, the calcium phosphate precipitation method of Graham et al., *Virology*, 52, 456–457 (1978) is preferred. Transformations into yeast are typically carried out according to the method of Van Solingen et al., *J. Bact.*, 130, 946 (1977) and Hsiao et al., *Proc. Natl. Acad. Sci.* (*USA*) 78 3829 (1979). However, other methods for introducing DNA into cells such as by nuclear injection, electroporation, or protoplast fusion may also be used.

5. Cell Culture

Prokaryotic cells used to produce the EST gene product, EST, are cultured in suitable media, as described generally in Sambrook et al. The mammalian host cells used to produce the EST gene product may be cultured in a variety of media. Commercially available media such as Hams F10 (Sigma), Minimal Essential Medium (MEM, Sigma), RPMI-1640 (Sigma), and Dulbecco's Modified Eagle's Medium (DMEM, Sigma) are suitable for culturing the host cells. These media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin' drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Induction of cells, to cause expression of the EST protein, is accomplished using the procedures required by the particular expression system selected. The host cells referred to in this disclosure encompass in in vitro culture as well as cells that are within a host animal. Cells are harvested, and cell extracts are prepared, using standard laboratory protocols. EST protein can be isolated from cell extracts. Optionally, cell extracts may be assayed directly for EST activity.

EST variants in which residues have been deleted, inserted, or substituted are recovered in the same fashion as native EST, taking account of any substantial changes in properties occasioned by the variation. For example, preparation of an EST fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal EST column can be employed to absorb the EST variant by binding it to at least one remaining immune epitope. Alternatively, the EST may be purified by affinity chromatography using a purified EST-IgG coupled to a (preferably) immobilized resin such as Affi-Gel 10 (Bio-Rad, Richmond, Calif.) or the like, by means well-known in the art. A protease inhibitor such as phenyl methyl sulfonyl fluoride (PMSF) also may be useful to inhibit proteolytic degradation during purification, and antibiotics may be included to prevent the growth of adventitious contaminants.

Estrogen sulfotransferase activity can be detected and quantified using an enzymatic assay. This assay can be used to measure EST activity in biological samples, preferably human samples, more preferably human liver preparations. It is sensitive and specific and can be used to detect the EST activity of any sulfotransferase, for example, human EST, DHEA ST and TS PST. The substrate used in the assay can be any estrogen or related chemical compound. Preferably, the substrate is estrone, estradiol-17β, ethinyl estradiol or dehydroepiandrosterone (DHEA). More preferably, estrone is used as the sulfate acceptor substrate in the assay. The assay contains estrone and a magnesium ($Mg^{2+}$) salt in a potassium phosphate buffer at a pH of about 6 to 7. Preferably, the assay mix contains 0.05 μM estrone, 0.25 mM $Mg^{2+}$ in 8.2 mM potassium phosphate buffer at pH 6.5.

Isolation and expression of a cDNA for human liver EST, and the development of an assay for EST activity, represent important steps toward understanding the biotransformation of estrogens in humans.

The invention has been described with reference to various specific and preferred embodiments and will be further described by reference to the following detailed examples. It is understood, however, that there are many extensions, variations and modifications on the basic theme of the present invention beyond that shown in the examples and detailed description, which are within the spirit and scope of the present invention.

EXAMPLES

Example I

PCR-based Cloning of Human Liver EST cDNA

1. Polymerase chain reaction (PCR) using rat EST cDNA as a probe. PCR was used to amplify the open reading frame (ORF) of rat liver EST cDNA. The rat liver PCR amplification product was subcloned, partially sequenced, and used as a probe to screen a human placental and two different human liver cDNA libraries. No positive clones were found.

2. Mixed oligonucleotide primed amplification of cDNA (MOPAC), and PCR using the resulting amplification product as a probe. Degenerate primers MOPAC1 and MOPAC2 (Table 1) were designed on the basis of the conserved mammalian amino acid sequences P(A/V)SFWEK SEQ ID NO:3 and HY(Q/E)QQMK (SEQ ID NO:4). The PCR was then performed in a 100 µl reaction volume (10 mM Tris, pH 8.3; 50 mM KCl; 1.5 mM $MgCl_2$; 0.01% gelatin; 50 µM each of the four deoxynucleoside triphosphates; and 1 unit of *Thermus aquaticus* DNA polymerase) in a Perkin Elmer Cetus DNA thermal cycler (Emeryville, Calif.) with human liver first strand cDNA as template. The amplification reaction conditions used, after initial denaturation for 10 minutes at 95° C., were 35 cycles of 1 minute at 94° C., 2 minutes at 48° C. and 3 minutes at 72° C., followed by a final 10 minutes incubation at 72° C. A 512 bp amplification product was obtained (FIG. 1). This amplification product was subcloned into pBluescript and was sequenced completely on both strands. This 512 bp product, corresponding to a portion of the coding region of a human EST cDNA, was then used to screen human liver, placenta and HepG2 hepatoma cell cDNA libraries, once again without success.

3. Direct PCR cloning of human EST cDNA. Anchored PCR then was performed using the rapid amplification of cDNA ends (RACE) (M. A. Frohman et al., *Proc. Natl. Acad. Sci. USA*, 85, 8998–9002 (1988)) protocol to directly obtain the remaining 5' and 3' terminal portions of human liver EST cDNA. The remaining 5'-portion of human liver EST cDNA was obtained using the EST specific primers 5'-RACE1 and 5'-RACE2 (Table 1 and FIG. 1). The 5'-AmpliFINDER RACE Kit (Clontech, Palo Alto, Calif.) was utilized to synthesize first-strand cDNA from human liver poly(A)+ RNA obtained from Clontech with 5'-RACE1 as a primer, followed by ligation of the 5'-ANCHOR ADAPTER. The PCR was then performed with 5'-RACE2 and 5'-ANCHOR PRIMER to yield an amplification product 533 nucleotides in length (FIG. 1). This product was sequenced with an Applied Biosystems automated DNA sequencer (Foster City, Calif.) in the Mayo Molecular Biology Core Resource Laboratory.

To obtain the 3'-end of the human liver EST cDNA, a 3'-RACE protocol was used with EST specific primers designated 3'-RACE1 and 3'-RACE2 (Table 1). First-strand cDNA synthesis was performed with 2 µg of total human liver RNA as template and the 3'-ANCHOR-d(T)$_{18}$ primer supplied with the first-strand cDNA Synthesis Kit (Pharmacia, Piscataway, N. J.). The PCR was then performed with this first-strand cDNA as template and 3'-RACE1 and 3'-ANCHOR-d(T)$_{18}$ as primers. An amplification product approximately 420 nucleotides in length was obtained, and this product was used as template for a nested PCR performed with 3'-RACE2 and 3'-ANCHOR-d(T)$_{18}$ as primers. The nested PCR yielded an amplification product 346 nucleotides in length (FIG. 1) that was sequenced using the fmol DNA Sequencing System (Promega, Madison, Wis.). Finally, PCR amplification of the entire EST cDNA coding region (885 bp, FIG. 1) was performed with the primers 5'-and 3'-ORF and with human liver cDNA as template (Table 1, FIG. 1).

This 885 bp amplification product was subcloned into the EcoRI sites of pBluescript and the eukaryotic expression vector p91023(B) (G. G. Wong et al., *Science*, 228, 810–815 (1985); R. J. Kaufman, *Proc. Natl. Acad. Sci. USA*, 82, 689–693 (1985)). These constructs were sequenced completely on both strands with the $^{35}$S-sequencing protocol of the Sequenase Kit version 2.0 (USB Corp., Cleveland, Ohio). The EST-pBluescript construct was linearized with KpnI, and a T3 RNA transcript was synthesized with the mCAP kit (Stratagene, La Jolla, Calif.).

TABLE 1

Primers used for PCR cloning of human liver EST cDNA. Restriction enzyme recognition sites incorporated into primer sequences are indicated by lines beneath appropriate sequences.

| Primer Designation | Primer Sequence |
|---|---|
| MOPAC1 (SEQ ID NO:5) | 5'-CCAG(C/T)(A/C)TCATTTTGGGAAAA-3' |
| MOPAC2 (SEQ ID NO:6) | 5'-TTCATTTGCTGCT(G/C)(A/G)TAGTG-3' |
| 5'-RACE1 (SEQ ID NO:7) | 5'-CCTGTCCTTGC ATGAATTTCTCCAC-3' |
| 5'-RACE2 (SEQ ID NO:8) | 5'-GATAGATTATCTTACAA-3' |
| 5'-ANCHOR ADAPTER (SEQ ID NO:9) | 5'-CACGAATTCACTATCGATTCTGGAACCTTCAGAGG-3'<br>EcoRI site |
| 5'-ANCHOR PRIMER (SEQ ID NO:10) | 5'-CTGGTTCGGCCCACCTCTGAAGGTTCCAGAATCGATAG-3' |
| 3'-RACE1 (SEQ ID NO:11) | 5'-GGGAAAGAGTCCACGTGT-3' |
| 3'-RACE2 (SEQ ID NO:12) | 5'-CCATCAGAGGAGCTTGTGGACAGG-3' |
| 3'-ANCHOR-d(T)$_{18}$ (SEQ ID NO:13) | 5'-AACTGGAAGAATTCGCGGCCGCAGGAA(T)$_{18}$-3' |
| 5'-ORF (SEQ ID NO:14) | 5'-AGTCCAATTGCAGTGTACCACAATGAATTCTG-3'<br>MunI site |
| 3'-ORF (SEQ ID NO:15) | 5'-GACTCAATTGCCTTCTTAGATCTCAGTTCGAA-3'<br>MunI site |

4. Results. Initial attempts to detect human EST DNA in human tissue were unsuccessful. First, PCR was used to amplify the entire open reading frame of a rat EST cDNA (subcloned from rat liver DNA). That amplification product was used as a probe to screen human placental and liver cDNA libraries in an effort to locate a human EST cDNA. No hybridizations were observed, suggesting that a homologous human EST cDNA was not present in these tissues.

Next, a PCR-based cloning strategy was adopted that utilized degenerate primers based on highly homologous nucleotide sequences present in the three reported non-human EST cDNAs (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol*, 6, 1216–1226 (1992)). This approach has been referred to as "mixed oligonucleotide primed amplification of cDNA" (MOPAC) (C. C. Lee et al., *Science*, 239, 1288–1291 (1988)). Two slightly degenerate (4-fold each) oligonucleotide primers (MOPAC1 and MOPAC2, Table 1) were used in a PCR with human liver cDNA as a template. An amplification product 512 nucleotides in length and encoding 170 amino acids (FIG. 1) was obtained. The encoded amino acid sequence was 85, 78 and 76% identical with sequences contained within guinea pig, bovine, and rat ESTs, respectively. This promising 512 bp amplification product was then used to probe the same three cDNA libraries that were probed with the rat liver EST amplification product, but despite the high homology of the 512 bp sequence to other mammalian ESTs, again no hybridization was observed.

Figure 3A:
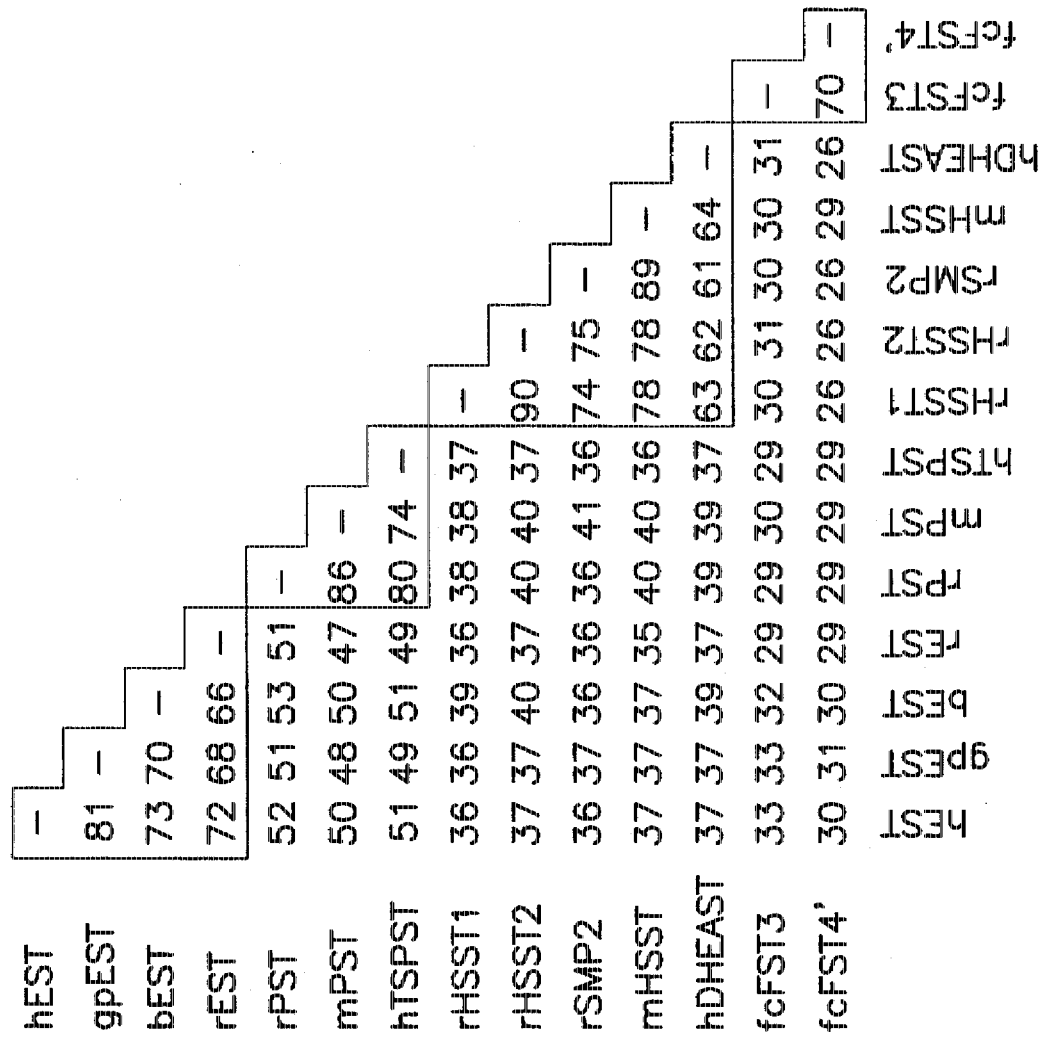
FIGS. 3 and 3B. A. Sequence identity among various known sulfotransferases. B. Dendogram relating various known sulfotransferases. The University of Wisconsin Genetics Computer Group software package was used to analyze sequence information and to make the comparisons among the sequences of ST cDNA.
Figure 3B:
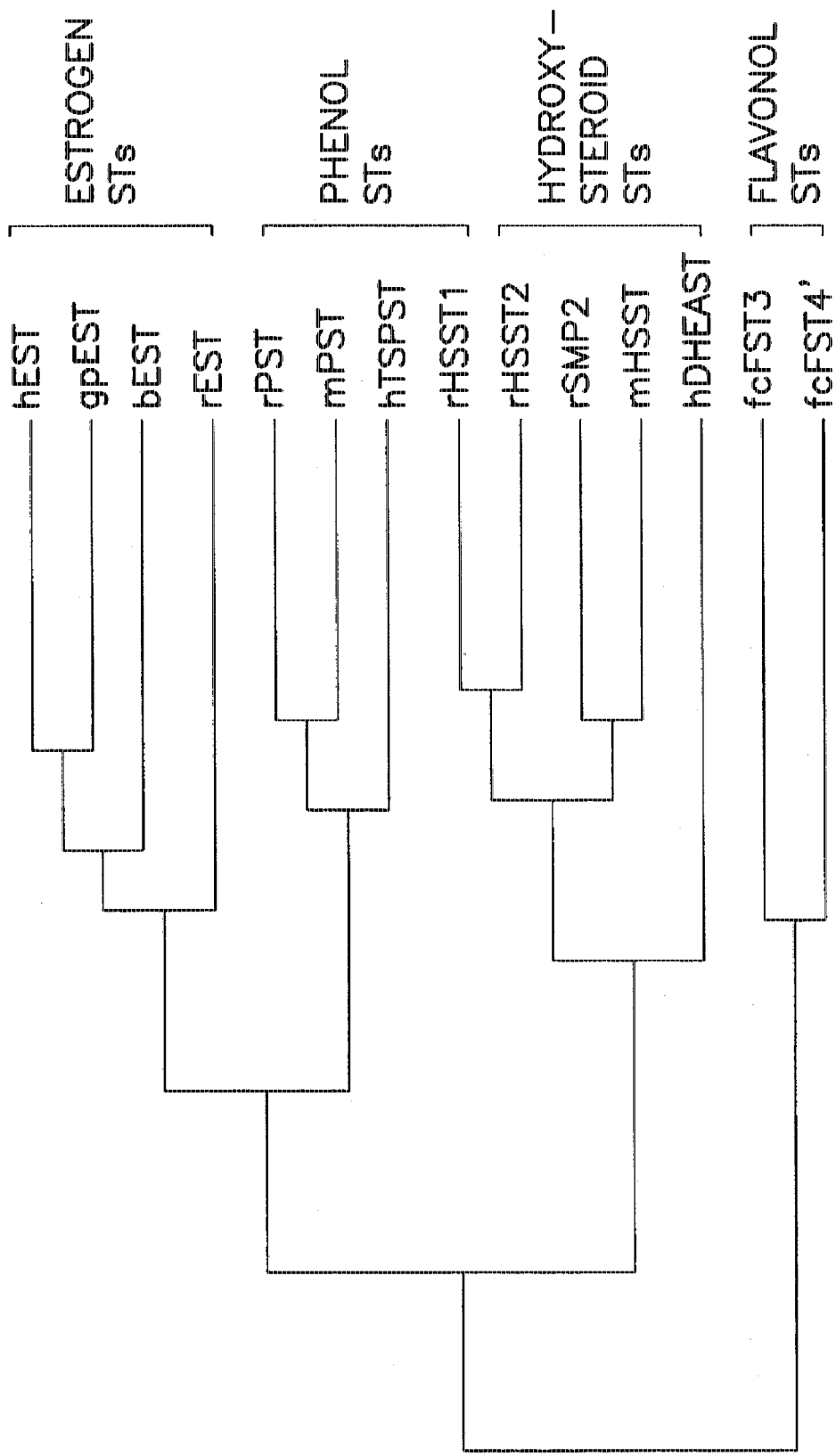

Success was finally achieved using a direct PCR-based cloning strategy to obtain the full length human EST cDNA. 5'-and 3'-RACE were used to obtain sequences 5' and 3' to the ends of the 512 bp product. 5'-RACE was employed to obtain the sequence of the remainder of the 5'-end of the coding region as well as the 5'-untranslated region (UTR). The 5'-UTR of the cDNA consisted of 106 nucleotides (FIG. 1). 3'-RACE was used to obtain the sequence of the 3'-end of the ORF as well as the 3'-UTR (Table 1, FIG. 1). The full length human liver EST cDNA consisted of 1063 nucleotides with an 882 nucleotide ORF that encodes 294 amino acids (FIG. 2) (SEQ ID NO:1 and SEQ ID NO:2). The 3'-UTR included 72 nucleotides and ended in a poly(A) tract. The polyadenylation signal ATTAAA was located 24 nucleotides upstream from the poly(A) tract (FIG. 2). The sequence of the protein encoded by this human liver EST cDNA was 81, 73 and 72% identical with the amino acid sequences of guinea pig adrenocortical, bovine placental, and rat liver ESTs, respectively (FIG. 3A) (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol.*, 6, 1216–1226 (1992)). However, it was only 37, 51 and 51% identical with the deduced amino acid sequences of human liver DHEA ST, TS PST and TL PST, respectively (FIG. 3A) (D. M. Otterness et al., *Mol. Pharmacol.*, 41, 865–872 (1992); T. W. Wilborn et al., *Mol. Pharmacol.*, 43, 70–77 (1993); T. C. Wood et al., *Biochem. Biophys. Res. Commun.*, 198, 1119–1127 (1994)). Comparison of the deduced amino acid sequence of EST with those of 13 other ST enzymes showed many areas of sequence homology, two of which have been observed to be highly conserved throughout phylogeny. One of those sequences, YPKSGTXW (SEQ ID NO:16), is located toward the amino, and the other, RKGXXGDWKNXFT (SEQ ID NO:17), toward the carboxy terminus of the proteins. Comparisons of percentages of amino acid sequence identities (FIG. 3A) and a dendrogram depicting graphically the relationships among these proteins (FIG. 3B) confirmed that the STs are a gene superfamily with striking sequence identity among orthologous enzymes across species lines.

Example II

Translation and Expression of Human Liver EST cDNA

A. In vitro transcription and translation. Transcription and translation of the 885 bp insert subcloned into pBluescript (Example I) was performed using the TnT Coupled Reticulocyte Lysate System (Promega Corp., Madison, Wis.). Translation products were analyzed by SDS-PAGE and autoradiography.

B. Expression in COS-1 cells. COS-1 cells were transfected with an EST cDNA expression construct in the eukaryotic expression vector p91023(B) as well as with vector alone using the DEAE-dextran method (H. Luthman et al., *Nucleic Acids Res.*, 11, 1295–1308 (1983)). After harvesting, cell pellets were washed with 5 ml of phosphate buffered saline (PBS) and were homogenized for 30 seconds in 2 ml of 5 mM potassium phosphate buffer, pH 6.5. The homogenates were centrifuged at 15,000×g for 15 minutes at 4° C., and supernatants were centrifuged at 100,000×g for 1 hour at 4° C. Five µl aliquots of the 100,000×g "high-speed supernatants" (HSS) were assayed for ST enzymatic activities.

C. Results. The insert subcloned into pBluescript (Example I) contained the entire coding region of the human liver EST cDNA. The major in vitro translation product had an apparent relative molecular weight ($M_r$) of 34.6 kDa estimated by sodium dodecyl sulfate-polyacrylamide gel electrophoresis (SDS-PAGE). The $M_r$ of human liver EST, calculated on the basis of amino acid sequence deduced from the sequence of the cDNA, was 35.1 kDa. ST activities were measured in preparations of transfected COS-1 cells using DHEA, 4-nitrophenol and dopamine, model substrates for DHEA ST, TS PST and TL PST, respectively. The protein encoded by the human liver EST cDNA was capable of catalyzing the sulfation of estrone (9 units/mg protein), DHEA (2.3 units/mg protein) and 4-nitrophenol (5 units/mg protein), but not that of dopamine. When transfection was performed with p91023(B) alone or with only buffer, no detectable ST activity was present with any of the substrates tested.

Example III

Development of an EST Assay

1. Identification of the preferred substrate for human EST. The protein encoded by the EST cDNA appeared to have greater ST enzyme activity when estrone was the sulfate acceptor substrate than was the case with estradiol-17β, ethinyl estradiol or DHEA.

2. Optimization of EST assay conditions. Estrone was used as the substrate to determine optimal assay conditions and, subsequently, to characterize the properties of human EST. A range of estrone concentrations from 0.01 to 0.10 µM was tested, and 0.05 µM gave maximal enzymatic activity. The optimal pH for the measurement of estrone ST activity with the expressed protein was approximately 6.5 in the presence of 8.2 mM potassium phosphate buffer. $Mg^{2+}$ increases the activities of several ST enzymes (J. S. Hernández, et al., *Drug Metab. Dispos.*, 20, 413–422 (1992); I. A. Aksoy et al., *Drug Metab. Dispos.*, 21, 268–276 (1993)). Therefore, a range of $Mg^{2+}$ concentrations from 0.04 to 10 mM was tested, and 1.25 mM $Mg^{2+}$ was found to increase EST activity 20% with estrone as a substrate. Subsequent EST assays were performed at a reaction pH of 6.5 in the presence of 1.25 mM $MgCl_2$ with 0.05 µM estrone as the sulfate acceptor substrate.

Example IV

Biochemical Characterization of Human EST

Biochemical characterization of human EST were carried out using aliquots of HSS from COS-1 cells transfected with human liver EST cDNA. Parallel experiments were performed with human liver DHEA ST cDNA (D. M. Otterness et at., *Mol. Pharmacol.*, 41, 865–872 (1992)) that had also been transiently expressed in COS-1 cells.

A. Sulfotransferase (ST) activities. The abilities of EST and DHEA ST to catalyze sulfation of various substrates were compared. ST activities were assayed by the method of Foldes and Meek (*Biochem. Biophys. Acta.*, 327, 365–374 (1973)), as modified by Hernandez et al. (*Drug Metab. Dispos.*, 20, 413–422 (1992)) for the measurement of human liver DHEA ST activity with its preferred substrate, DHEA, and by Campbell et al. (*Biochem. Pharmacol.*, 36, 1435–1446 (1987)) for the measurement of human liver TS and TL PST activities with their preferred substrates, 4-nitrophenol and dopamine, respectively. These assays were performed under optimal conditions for the measurement of ST enzyme activities in human liver preparations (N. R. C. Campbell et al., *Biochem. Pharmacol.*, 36, 1435–1446 (1987); J. S. Hernandez et al., *Drug Metab. Dispos.*, 20, 413–422 (1992). For the measurement of estrone sulfating activity, the optimized assay conditions described in Example III were used. Specifically, the sulfate acceptor substrates used in the various assays were DHEA (5 µM), 4-nitrophenol (4 µM), dopamine (60 µM), and estrone (0.05 µM), respectively. Controls did not contain sulfate acceptor substrates.

One unit of enzyme activity represented the formation of 1 nmol of sulfated product per hour of incubation at 37° C. All assays were performed in triplicate, and values reported are averages of those three determinations. Protein concentrations were measured by the method of Bradford (*Anal. Biochem.*, 72, 248–254 (1976)) with bovine serum albumin as a standard.

B. Kinetics of ST activity. Substrate kinetic studies designed to estimate apparent $K_m$ values were performed. Since human liver EST and DHEA ST can both catalyze the sulfation of steroids, these studies presented an opportunity to determine apparent $K_m$ values of the two enzymes with estrone and DHEA as substrates. Both enzyme preparations were tested with a range of estrone and DHEA concentrations. Apparent $K_m$ values for the sulfation of estrone and DHEA catalyzed by human liver EST calculated from these data were 0.17 and 0.85 µM, respectively, while those for reactions catalyzed by human liver DHEA ST were 3.1 and 2.6 µM, respectively. Apparent $K_m$ values were calculated by the method of Wilkinson (*Biochem. J.*, 80, 324–332 (1961)) with a computer program written by Cleland (*Nature*, 198, 463–465 (1963)).

Figure 4A:
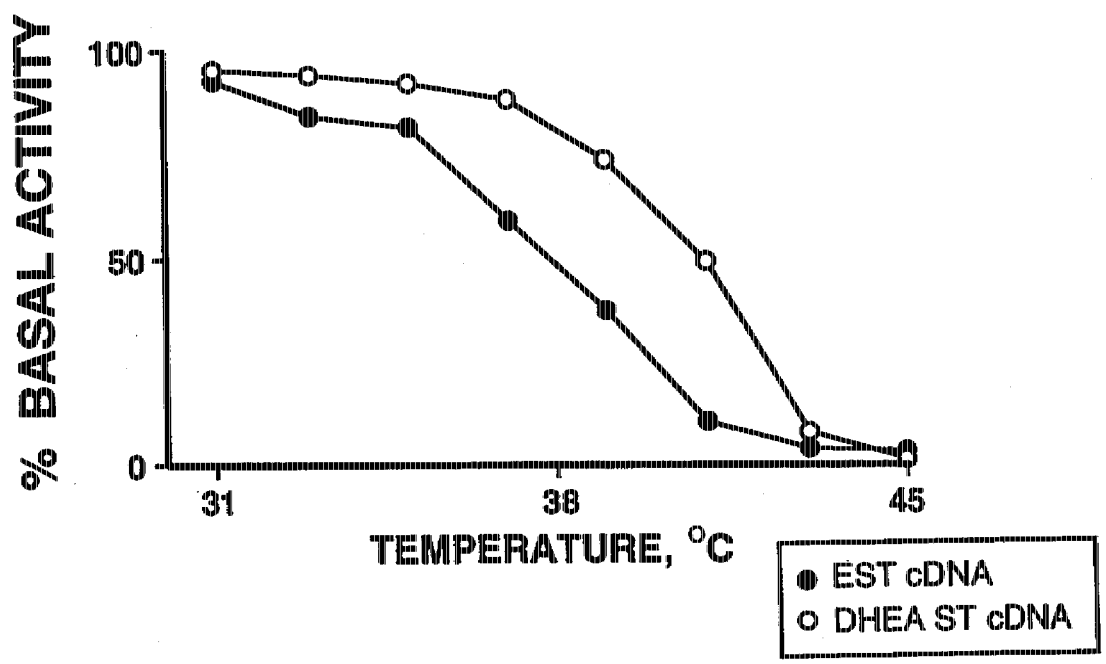
FIG. 4. Response of EST (closed circles) and DHEA ST (open circles) cDNAs expressed in COS-1 cells to changes in (A) temperature; (B) DCNP concentration; and (C) NaCl concentration. Each point is the mean of three determinations.

C. Thermal inactivation of ST activity. Thermal stability is a sensitive indicator of differences in protein structure and the thermal stabilities of the three well-characterized STs present in the human liver differ dramatically (R. M. Weinshilboum et al., *Conjugation-Deconjugation Reactions in Drug Metabolism and Toxicity*, "Handbook of Experimental Pharmacology" series, R. C. Kauffman, Ed., Springer-Verlag (1994)). The temperatures at which 50% inactivation of EST (using its preferred substrate, estrone) and DHEA ST (using its preferred substrate, DHEA) activities occurred were 38.2±0.12 (mean±SEM) and 41.1±0.10° C., respectively (FIG. 4A). For the thermal inactivation experiment, HSS from COS-1 cells transfected with EST cDNA or DHEA ST cDNA was diluted 1:2 (v/v) with 5 mM potassium phosphate buffer, pH 6.5, preincubated at various temperatures for 15 minutes and was then placed on ice. An aliquot of the same preparation was kept on ice as a control. Each aliquot was then diluted further for assay of the ST activity being measured. Values for controls were determined at each temperature studied. The results are reported in FIG. 4A.

Figure 4B:
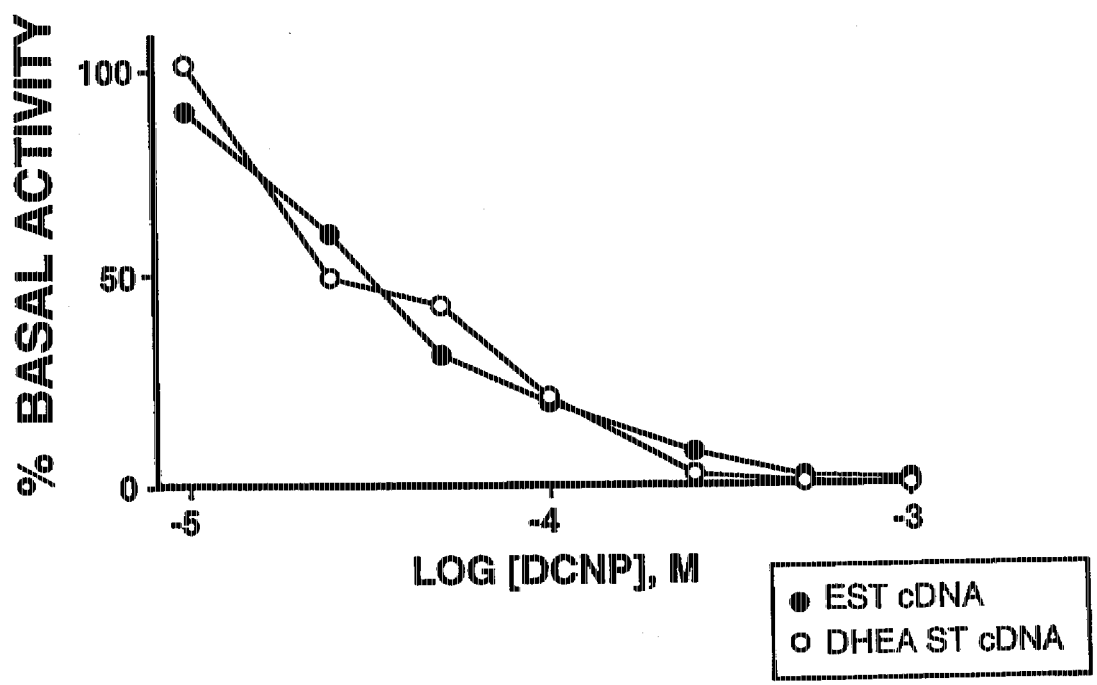

D. DCNP inhibition of EST activity. DCNP is a competitive inhibitor of ST enzymes (G. Rein et al., *Biochem. Pharmacol.*, 31, 1893–1897 (1982)), and DCNP inhibition profiles of human liver ST enzymes can differ greatly (R. M. Weinshilboum et al., *Conjugation-Deconjugation Reactions in Drug Metabolism and Toxicity*, "Handbook of Experimental Pharmacology" series, R. C. Kauffman, Ed., Springer-Verlag (1994)). EST activity (using its preferred substrate, estrone) and DHEA ST activity (using its preferred substrate, DHEA) were 50% inhibited at very similar mean DCNP concentrations, 28±2.9 and 40±2.3 µM, respectively (FIG. 4B).

Figure 4C:
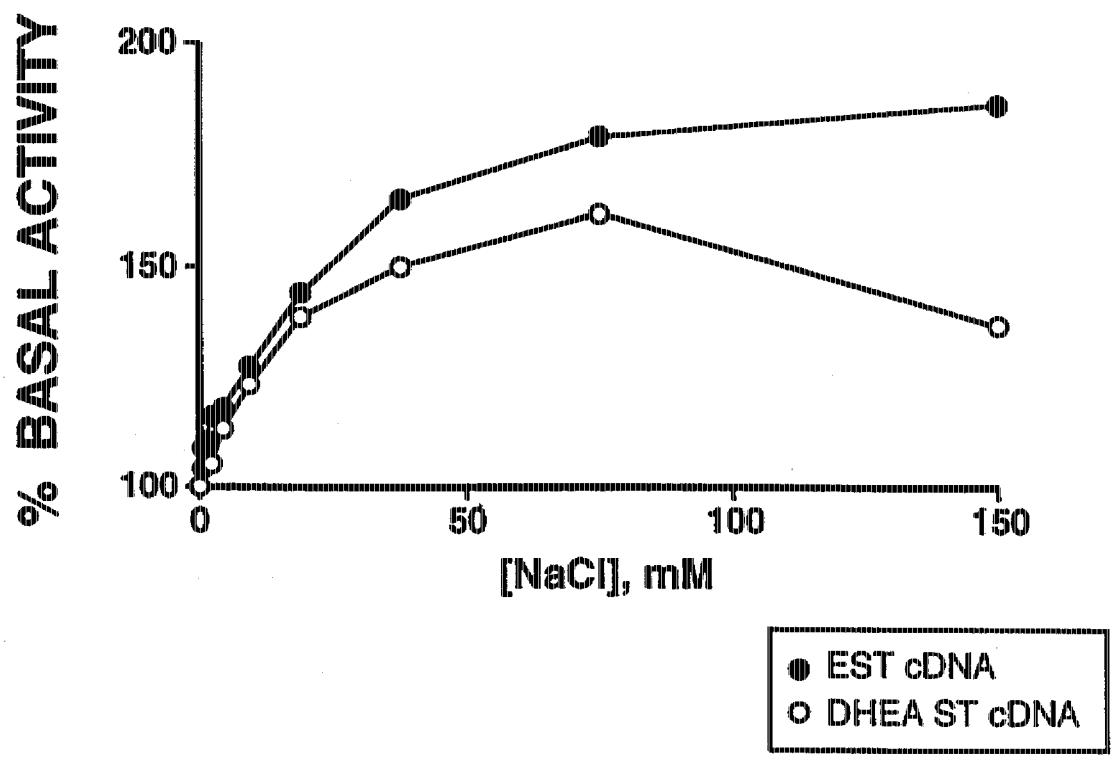

E. Effect of NaCl concentration on EST activity. NaCl also has differential effects on ST enzyme activities in human liver (R. M. Weinshilboum et al., Conjugation-Deconjugation Reactions in Drug Metabolism and Toxicity, "Handbook of Experimental Pharmacology" series, R. C. Kauffman, Ed., Springer-Verlag (1994); I. A. Aksoy et al., *Drug Metab. Dispos*, 21, 268–276 (1993)). Human liver EST activity (using its preferred substrate, estrone) transiently expressed in COS-1 cells increased 86% in the presence of 150 mM NaCl, while peak activation for human liver DHEA ST (using its preferred substrate, DHEA) of 62% occurred in the presence of 75 mM NaCl (FIG. 4C).

F. Northern and Southern blot analyses. Northern blot analysis performed with poly(A)⁺ RNA and with the ORF of human liver EST cDNA as a probe showed the presence, in both liver and placenta, of a transcript approximately 2 kb in length. Liver also showed a transcript approximately 1.2 kb in length and the possible existence of an even shorter mRNA species. Southern blot analysis of human lymphocyte DNA was performed with the same probe. Only one or very few copies of the gene(s) for human liver EST appeared to be present in the human genome.

It will be appreciated by those skilled in the art that various modifications can be made to the above described embodiments of the invention without departing from the essential nature thereof. The invention is intended to encompass all such modifications within the scope of the appended claims. All publications, patents, and patent documents are incorporated by reference herein, as though individually incorporated by reference.

What is claimed is:

1. An isolated and purified DNA molecule comprising a DNA segment having a nucleotide sequence that encodes a human estrogen sulfotransferase having the amino acid sequence of SEQ ID NO:2, or a biologically active fragment of said human estrogen sulfotransferase.

2. The DNA molecule of claim 1 wherein the DNA segment encodes a human estrogen sulfotransferase having the amino acid sequence of SEQ ID NO:2.

3. The DNA molecule of claim 2 wherein the DNA segment has the nucleotide sequence of SEQ ID NO:1.

4. The DNA molecule of claim 1 wherein the DNA segment encodes a biologically active fragment of a human estrogen sulfotransferase wherein the human estrogen sulfotransferase has the amino acid sequence of SEQ ID NO:2.

5. An isolated and purified DNA molecule for use in recombinant DNA technology comprising:

(a) a single coding region having a nucleotide sequence that encodes a human estrogen sulfotransferase having the amino acid sequence of SEQ ID NO:2, or a biologically active fragment of said human estrogen sulfotransferase;

(b) a 5' untranslated region; and (c) a 3' untranslated region.

6. The DNA molecule of claim 5 wherein the single coding region encodes a human estrogen sulfotransferase having the amino acid sequence of SEQ ID NO:2.

7. The DNA molecule of claim 6 wherein the single coding region has the nucleotide sequence of SEQ ID NO:1.

8. The DNA molecule of claim 5 wherein the single coding region encodes a biologically active fragment of a human estrogen sulfotransferase wherein the human estrogen sulfotransferase has the amino acid sequence of SEQ ID NO:2.

9. The DNA molecule of claim 5 wherein the 5' untranslated region comprises a promoter region operably linked to the 5' end of the single coding region.

* * * * *

UNITED STATES PATENT AND TRADEMARK OFFICE
CERTIFICATE OF CORRECTION

| | |
|---|---|
| PATENT NO. | : 5,714,594 |
| APPLICATION NO. | : 08/325562 |
| DATED | : February 3, 1998 |
| INVENTOR(S) | : Weinshilboum et al. |

It is certified that error appears in the above-identified patent and that said Letters Patent is hereby corrected as shown below:

In column 1, line 5, above "BACKGROUND OF THE INVENTION" insert

-- This invention was made with government support under GM028157 and GM035720 awarded by National Institutes of Health. The government has certain rights in the invention. --.

Signed and Sealed this

Twenty-fifth Day of December, 2007

JON W. DUDAS
*Director of the United States Patent and Trademark Office*